(12) United States Patent
Berthaud et al.

(10) Patent No.: US 7,231,462 B2
(45) Date of Patent: Jun. 12, 2007

(54) METHOD OF PRESERVING SYMMETRICAL ROUTING IN A COMMUNICATION SYSTEM BASED UPON A SERVER FARM

(75) Inventors: Jean-Marc Berthaud, Villeneuve Loubet (FR); Pascal Chauffour, Cagnes sur Mer (FR); Jean-Claude Dispensa, Saint Jeannet (FR); Valerie Mahe, Nice (FR)

(73) Assignee: International Business Machines Corporation, Armonk, NY (US)

( * ) Notice: Subject to any disclaimer, the term of this patent is extended or adjusted under 35 U.S.C. 154(b) by 942 days.

(21) Appl. No.: 10/317,652

(22) Filed: Dec. 12, 2002

(65) Prior Publication Data

US 2003/0126268 A1 Jul. 3, 2003

(30) Foreign Application Priority Data

Dec. 21, 2001 (EP) .................................. 01480137

(51) Int. Cl.
G06F 15/173 (2006.01)
G06F 15/16 (2006.01)
H04L 12/28 (2006.01)
H04L 12/56 (2006.01)

(52) U.S. Cl. ........................ 709/249; 709/240; 370/401
(58) Field of Classification Search ................ 709/203, 709/219, 240, 249; 370/395.3, 401
See application file for complete search history.

(56) References Cited

U.S. PATENT DOCUMENTS

| 6,173,311 | B1 | 1/2001 | Hassett et al. .............. 709/202 |
| 6,397,260 | B1* | 5/2002 | Wils et al. ................... 709/238 |
| 6,556,547 | B1* | 4/2003 | Srikanth et al. ............. 370/317 |
| 6,885,633 | B1* | 4/2005 | Mikkonen .................... 370/217 |
| 2002/0145981 | A1* | 10/2002 | Klinker et al. .............. 370/244 |
| 2003/0120816 | A1 | 6/2003 | Berthaud et al. ........... 709/248 |
| 2003/0126268 | A1 | 7/2003 | Berthaud et al. ........... 709/229 |
| 2003/0131262 | A1* | 7/2003 | Goddard ..................... 713/201 |

FOREIGN PATENT DOCUMENTS

EP 1 035 708 A1 9/2000

OTHER PUBLICATIONS

S. Knight et al. "Request for Comments (RFC) 2338: Virtual Router Redundancy Protocol", published by Network Working Group, Apr. 1998, 27 pages.*

(Continued)

Primary Examiner—David Wiley
Assistant Examiner—George C. Neurauter, Jr.
(74) Attorney, Agent, or Firm—David L. Adour; Hoffman, Warnick & D'Alessandro LLC

(57) ABSTRACT

A method of preserving symmetrical routing in a communication system comprising a server farm connected to the Internet by an Internet access router IAR. The server farm includes at least two customer cabinets each having a WEB server, and at least two firewalls. The firewalls use Virtual Router Redundancy Protocol (VRRP) to set up a primary firewall that supports communication between a customer server and an Internet user. The IAR selects the firewall to be used as being the firewall corresponding to the interface having the lowest weight in a routing table. The cost assigned to each interface associated with a firewall is automatically generated, at the initial time, according to the priority assigned by the VRRP protocol to said interface associated with said firewall.

9 Claims, 3 Drawing Sheets

OTHER PUBLICATIONS

Berthaud, J. et al. "Method of Preserving Symmetrical Routing in a Communication System Based Upon a Server Farm", IBM Patent Application, IBM Docket No. FR920010019US1, Filed concurrently with this application.

* cited by examiner

METHOD OF PRESERVING SYMMETRICAL ROUTING IN A COMMUNICATION SYSTEM BASED UPON A SERVER FARM

TECHNICAL FIELD

The present invention relates to communication systems wherein customer cabinets containing customer WEB servers are hosted in a server farm connected to the Internet network, and relates in particular to a method of preserving symmetrical routing in such a communication system.

BACKGROUND

A server farm is a physical location having a scalable infrastructure and facilities and resources enabling users connected to the Internet network to easily access a number of services provided by a plurality of customers hosted by the server farm. Generally, the resources are located in premises owned by a data processing equipment provider such as the IBM Corporation.

Most server farms are used today to host Internet related devices (for example WEB servers) of several customers. The architecture of such a server farm includes a local network to which are connected the customer cabinets and an Internet front-end connecting this local network to the Internet. Such a local network includes different layers of components such as switches and firewalls through which the requests from the users connected to the Internet are routed towards the customer cabinets.

The firewalls are intermediary devices between the local Network and the front-end. They are connected by a LAN to an Internet Access Router (IAR) which is directly connected to the Internet.

The firewalls present all the characteristics of a router with the addition of security filtering features known as firewall rules. Firewalls also have the capability to inspect IP packets and track the state of sessions going through the firewall and established between any of two devices separated by this firewall. This capability, which is known as "Statefull Inspection", includes checking that every backward connection is associated with an existing forward connection and following the state of a connection to allow only packets that are in the right sequence level of the connection to proceed. This means that, if a connection is established from an end user to a WEB server (forward path) through a first firewall, all the responses coming from the WEB server to the end user (reverse path) will have to go through this firewall. If any firewall receives a reverse path frame without having received a forward path frame, it will drop the reverse frame. If any firewall receives a data packet while the session is only at the connecting state, it will drop the data packet.

In the local network, a protocol such as the Virtual Route Routing Protocol (VRRP) is used between the firewalls. VRRP allows the customer WEB servers to see the redundant firewalls as a single virtual firewall. At any instant and on a per customer basis, only one firewall really owns the virtual firewall function based on the availabilities of the firewall interfaces or on static priorities associated with them by configuration. The individual interface to a customer cabinet having the highest priority is the one elected to own the virtual firewall interface. The associated firewall acts as the virtual firewall until it fails or until another interface with a higher priority appears. A first firewall (also called the primary firewall) can own the virtual firewall function for a subset of the customer servers while the other firewall (also called the secondary firewall) can own this role for another set of customers. In other words, the first firewall owns the primary interface of the VRRP group of interfaces to each one of these customer servers.

In the context of the invention, the customer servers are not allowed to communicate with each other. However, the customer servers hosted in the cabinets can plug, and unplug the link to the firewalls on their own, thereby impacting all the other attached customer servers if all the customer servers were switched at once. There could be a situation where all the customer servers would flip-flop permanently between firewalls just because of one customer server putting its links up and down.

Accordingly, and as no connections between customer servers are allowed, the requirement is to switch only one customer server in case of link failure and to configure the firewalls so that one firewall is the primary firewall for half the customer servers whereas another firewall is primary for the other half of the customer servers. Sharing the initial load between the firewalls at startup time improves the response time and the performance of the system as it avoids end-to-end retransmission when a frame is lost in the firewall because of temporary congestion. Such a load sharing is done in configuring adequately the priorities of the different interfaces by VRRP in each firewall.

But there is still a problem if there is a failure of the interface between a customer server and the firewall which is the primary firewall for this interface. In such a case, the secondary firewall detects the failure by the internal mechanism of VRRP and becomes the primary firewall. Nevertheless, the traffic from the IAR to the customer server which keeps on using the first firewall is cut since the interface between this firewall and the customer server has failed. It is therefore necessary to force the traffic from the IAR to the customer server to be routed through the second firewall in order to preserve the symmetrical routing for this customer server.

SUMMARY

Accordingly, an object of the invention is to achieve a method of preserving symmetrical routing, in a communication system including a server farm connected to the Internet network by the intermediary of at least two redundant firewalls, when an interface fails between a customer server and the firewall being currently used.

Another object of the invention is to achieve a method of preserving symmetrical routing in a communication system as above when there is a failure between a customer server and a firewall, by switching this customer server to another firewall whereas the other customers servers keep using the first firewall.

The invention relates therefore to a method of preserving symmetrical routing in a communication system that includes a server farm connected to the Internet network by an Internet front-end including at least an Internet access router IAR. The server farm includes at least two customer cabinets, with each customer cabinet including at least a WEB server and server farm resources enabling any user connected to the Internet network to access the WEB servers in the customer cabinets, and at least two firewalls for controlling any communication between any user and one WEB server. The firewalls use a Virtual Router Redundancy Protocol (VRRP) or the like to set up as primary firewall the firewall which owns the primary interface of the VRRP group of interfaces to at least one customer server and through which is established any communication from one customer server and an Internet user, and the IAR selecting the firewall to be used in any communication from an Internet user to any one of the Internet users as being the firewall corresponding to the link having the lowest weight in a routing table. The weight assigned to each link associated to a firewall is automatically generated, at the initial time, according to the priority assigned by the VRRP protocol to the link associated with this firewall.

BRIEF DESCRIPTION OF THE DRAWINGS

The above and other objects, features and advantages of the invention will be better understood by reading the following more particular description of the invention in conjunction with the accompanying drawings wherein.

DETAILED DESCRIPTION

The invention as described herein results from a coupling between the VRRP protocol in charge of the links between the firewalls and the customer servers and another protocol OSPF (Open Shortest Path First). OSPF is a routing protocol used between the firewalls and the IAR used to dynamically exchange and propagate routing information in such a manner that the IAR sending a packet to a customer server is able to associate with each firewall a cost for reaching the customer server and then to choose one firewall having the lowest cost as being the next hop to forward this packet.

Figure 1:
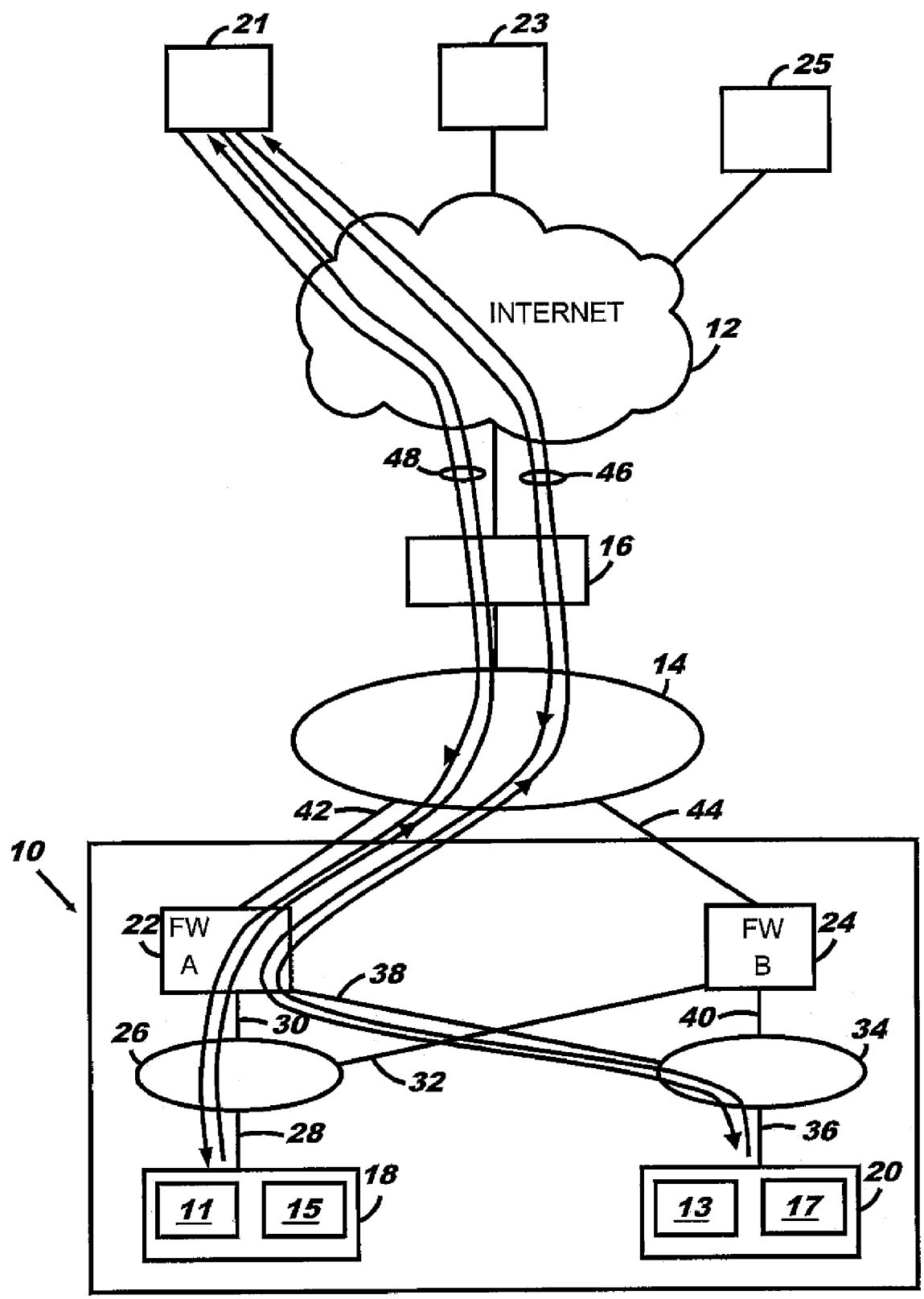
FIG. 1 is a schematic block-diagram representing a communication system showing flow paths between an Internet user and two customer servers.

The method according to the invention may be implemented in the context illustrated in FIG. 1 wherein a server farm 10 is connected to the Internet network 12 (or any other Intranet network) by the intermediary of a LAN 14 and an Internet Access Router (IAR) 16. Several customer cabinets such as cabinets 18 and 20 are hosted in server farm 10, each cabinet including one or several customer WEB servers 11 and 13 and server farm resources 15 and 17. Each customer cabinet is connected to at least two firewalls 22 and 24 by the intermediary of switches. Thus, customer cabinet 18 is physically connected to a switch 26 by a link 28, the switch 26 being physically connected to firewall 22 by a link 30 and to firewall 24 by a link 32. Likewise, customer cabinet 20 is physically connected to a switch 34 by a link 36, the switch 34 being physically connected to firewall 22 by a link 38 and to firewall 24 by a link 40. Finally, firewalls 22 and 24 are physically connected to LAN 14 by respective links 42 and 44. Note that a plurality of users such as user 21, 23 and 25 can send requests to the customer WEB servers 11 and 13 of each cabinet 18 or 20.

In the communication system illustrated in FIG. 1, the customer servers 11 and 13 included in cabinets 18 and 20 are reached by two different flow paths 46 and 48 going though firewall 22. Thus, cabinet 18 is reached from the LAN 14 through links 42, 30 and 28 whereas cabinet 20 is reached from the LAN 14 through links 42, 38 and 36. It must be noted that because of the Stateful Inspection mode in the firewalls, the forward path for each At the initial time and thanks to the initial VRRP configuration, each firewall such as firewall A 22 or firewall B 24 represented in FIG. 1 has an internal table as follows.

| Firewall A | Interface to | VRRP priority |
|---|---|---|
| | Cabinet 18 | High |
| | Cabinet 20 | High |

| Firewall B | Interface to | VRRP priority |
|---|---|---|
| | Cabinet 18 | Low |
| | Cabinet 20 | Low |

At the initial time and thanks to the initial OSPF protocol configuration, a cost for reaching each cabinet is normally assigned to each interface in each firewall. The principle of the invention is to have such an OSPF cost automatically generated by a script program based upon the VRRP priorities. In the present example, it is assumed that the cost for the two firewalls are as follows:

| Firewall A | | |
|---|---|---|
| Interface to | VRRP priority | OSPF cost |
| Cabinet 18 | High | 1 |
| Cabinet 20 | High | 1 |

| Firewall B | | |
|---|---|---|
| Interface to | VRRP priority | OSPF cost |
| Cabinet 18 | Low | 10 |
| Cabinet 20 | Low | 10 |

Figure 2:
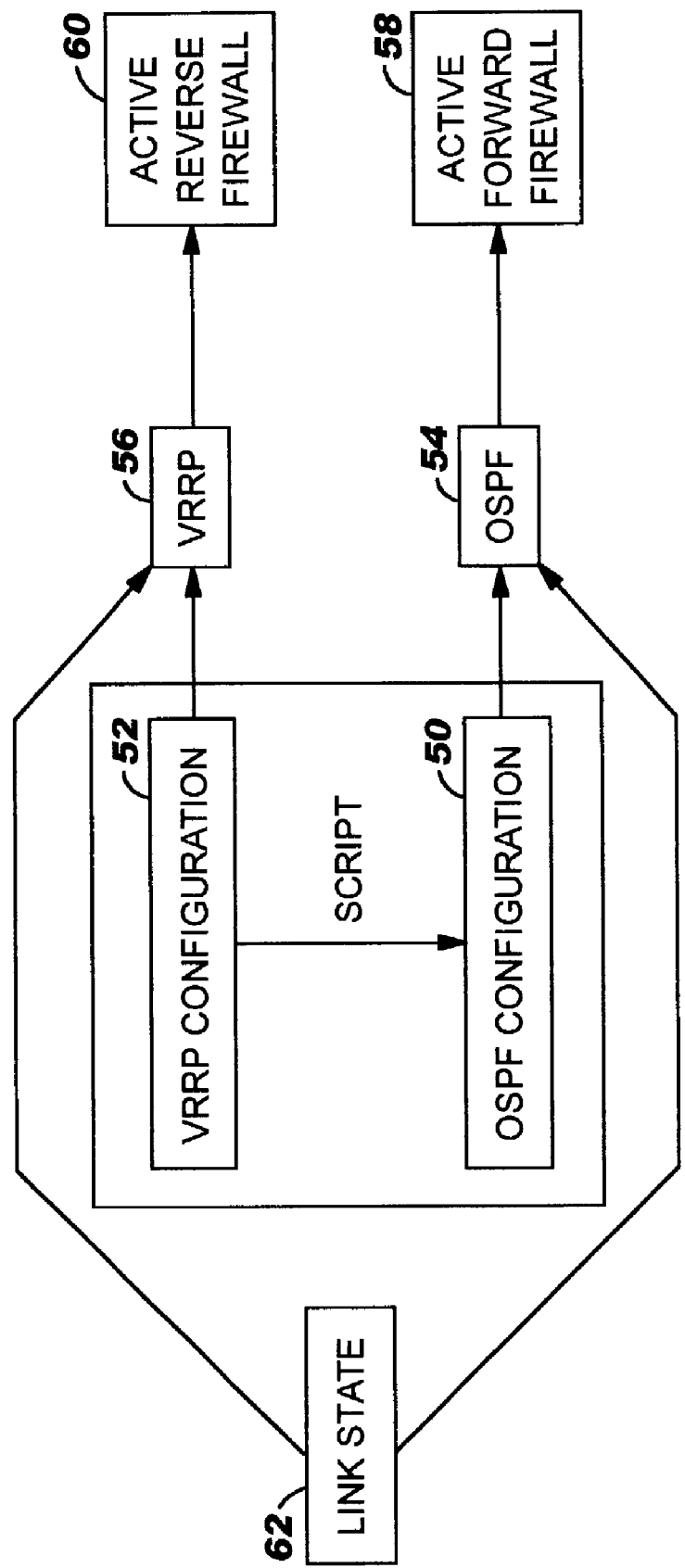
FIG. 2 is a schematic block-diagram illustrating the different features involved in the invention.

Such an automatic generation is illustrated in FIG. 2 wherein the OSPF configuration 50 at the initial time results from the VRRP configuration 52 by application of a "script" represented by an arrow.

Always at the initial time, the IAR receives from each firewall the OSPF costs assigned to each interface generated as mentioned above and sets up a routing table giving the next hop to be used in view of weights which are assigned to each interface and which result from the generated costs. To simplify, these weights have the same value as the corresponding costs in the following table:

| Interface to | Next hop | OSPF weight |
|---|---|---|
| Cabinet 18 | Firewall A | 1 |
| | Firewall B | 10 |
| Cabinet 20 | Firewall A | 1 |
| | Firewall B | 10 |

At each instant, as illustrated in FIG. 2, the OSPF protocol 54 as well as the VRRP protocol 56 selects the firewall to be used, that is the active forward firewall 58 for a connection from an Internet user to the cabinet and the active reverse firewall 60 for the reverse connection from the cabinet to the Internet user.

Such a dynamic selection is performed by using two input parameters: the initial configuration and the current state 62 of the link being considered. Such a state can be defined as "up" when the link is operational and "down" when the link has failed. Thus, for the VRRP, if the state of a link changes from up to down, the secondary firewall for this link becomes the active firewall for this link as primary firewall whereas the primary firewall becomes the secondary firewall for this link, bearing in mind that a firewall is considered as primary when it owns the primary link of the VRRP group of links to the customer server 11 or 13 being considered. For the OSPF protocol, a solution includes assigning an "infinite" weight to the link which has failed.

In the present example, assuming that the link 38 between cabinet 20 and firewall A 22 fails, the firewall B 24 becomes the primary firewall for the cabinet 20 from a VRRP point of view. This means that all the frames from cabinet 20 will now go through firewall B 24 while all the frames from cabinet 18 keeps on going through firewall A 22 which is still the primary firewall for cabinet 18. On the other hand, since link 38 has failed, its weight associated with firewall A 22 becomes infinite from an OSPF point of view. Therefore the routing table in the IAR becomes as follows:

| Interface to | Next hop | OSPF weight |
|---|---|---|
| Cabinet 18 | Firewall A | 1 |
|  | Firewall B | 10 |
| Cabinet 20 | Firewall A | infinite |
|  | Firewall B | 10 |

Accordingly, the IAR 16 will automatically use firewall A 22 for cabinet 18 (the OSPF weight is 1) and firewall B 24 for cabinet 20 (weight is 10 lower than infinite).

Figure 3:
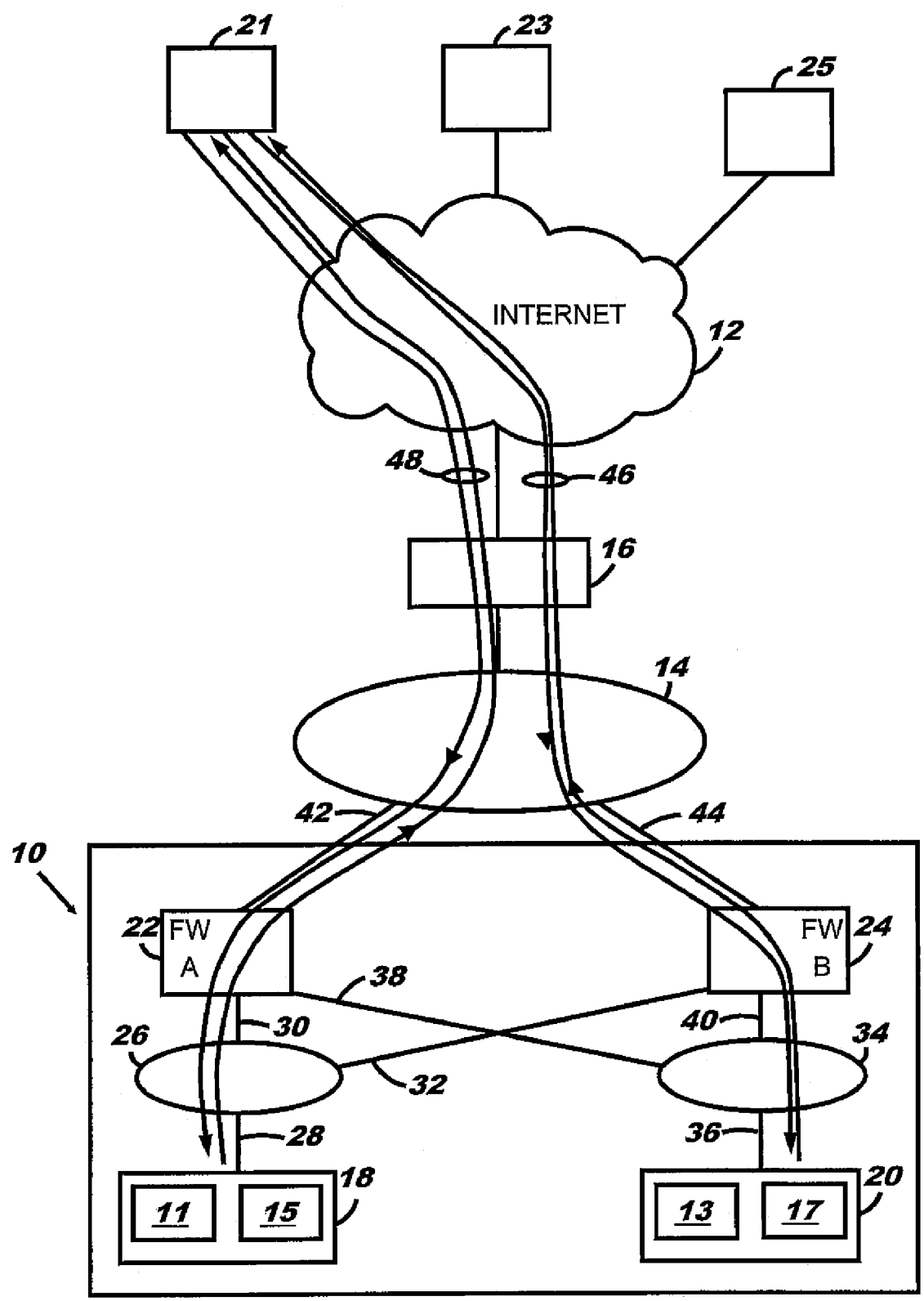
FIG. 3 is a schematic block-diagram representing the same communication system as FIG. 1 wherein are shown the flow paths between the Internet user and the two customer servers after failure of a link with one of these customer servers.

Therefore, symmetrical routing is preserved here as both forward and reverse paths for cabinet 20 are now through firewall B 24 as illustrated in FIG. 3. This solution allows switching one cabinet at a time for both forward and reverse paths in case of a link failure while keeping the other cabinets untouched.

We claim:

1. A method of preserving symmetrical routing in a communication system comprising a server farm connected to the Internet network by an Internet front-end including at least an Internet access router IAR, said server farm comprising at least two customer cabinets with each customer cabinet including at least a web server and server farm resources enabling users connected to the Internet to access the WEB servers in said customer cabinets, and at least two firewalls for controlling communication between users and one of said WEB servers, said firewalls using a Virtual Router Redundancy Protocol (VRRP) to set up a primary firewall which owns the primary link of the VRRP group of links to at least one customer server and though which is established communication from said customer server and an Internet user, and said IAR selecting a firewall to be used in any communication from an Internet user to any one of said Internet users as being the firewall corresponding to the link having the lowest weight in a routing table;

said method comprising the step of automatically generating a cost assigned to each of a plurality of interfaces associated with the at least two firewall, at an initial time, according to a priority assigned by the VRRP protocol to said interface associated with said firewall.

2. The method according to claim 1, wherein aweight assigned to each link associated with a firewall is established according to a cost for reaching each of said cabinets, said cost being associated with each firewall.

3. The method according to claim 2, wherein said IAR selects, at the initial time, a firewall which is associated with the lowest weight for reaching any one of said cabinets.

4. The method according to claim 3, wherein the weight assigned to a link becomes infinite when said link fails.

5. The method according to claim 1, wherein the VRRP protocol selects a firewall as being the primary firewall for a link from one of said cabinets to said firewall which has the highest priority.

6. The method according to claim 5, wherein said firewall becomes a secondary firewall when said link fails.

7. A computer program product stored on a computer readable medium for preserving symmetrical routing in a communication system comprising instructions adapted to implement the method according to claim 1.

8. A communication system comprising a server farm connected to the Internet network by an Internet-front end including at least an Internet access router, said server farm comprising at least two customer cabinets with each customer cabinet including at least a WEB server and server farm resources enabling users connected to the Internet to access the WEB servers in said customer cabinets, and at least two firewalls for controlling communication between users and one of said WEB servers, said firewalls using a Virtual Router Redundancy Protocol (VRRP) to setup one of said firewalls as being a primary firewall through which is established communication between an Internet user and one of said customer servers wherein each one of said firewalls is provided with a computer program according to claim 7.

9. A communication system according to claim 8, wherein each of said firewalls runs a Statefull Inspection program in order to verify that connections between an Internet user and one of said customer servers have symmetrical routing.

* * * * *